United States Patent [19]

Ertel

[11] 4,229,349
[45] Oct. 21, 1980

[54] PRODUCTION OF SEMI-SYNTHETIC β-LACTAM ANTIBIOTICS

[75] Inventor: Werner Ertel, Wuppertal, Fed. Rep. of Germany

[73] Assignee: Bayer Aktiengesellschaft, Leverkusen, Fed. Rep. of Germany

[21] Appl. No.: 27,539

[22] Filed: Apr. 5, 1979

[30] Foreign Application Priority Data

Apr. 20, 1978 [DE] Fed. Rep. of Germany ....... 2817228

[51] Int. Cl.$^2$ .................. C07D 499/12; C07D 501/06
[52] U.S. Cl. .................................. 260/239.1; 544/21; 544/27; 544/28
[58] Field of Search ................ 260/239.1; 544/28, 21, 544/27

[56] References Cited

U.S. PATENT DOCUMENTS

| | | | |
|---|---|---|---|
| 3,864,329 | 2/1975 | Tobiki et al. | 260/239.1 |
| 4,015,000 | 3/1977 | Kocsis et al. | 260/239.1 |
| 4,039,673 | 8/1977 | Konig et al. | 544/28 X |
| 4,053,609 | 10/1977 | Kawazu et al. | 260/239.1 |
| 4,087,424 | 5/1978 | Saikawa et al. | 260/239.1 X |

*Primary Examiner*—Natalie Trousof
*Assistant Examiner*—Vera C. Clarke
*Attorney, Agent, or Firm*—Sprung, Felfe, Horn, Lynch & Kramer

[57] ABSTRACT

In the production of a semi-synthetic β-lactam antibiotic by reacting an amino compound of the formula

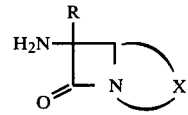

in which
 X is the remaining members of a ring of a β-lactam antibiotic, and
 R is a hydrogen atom or a methoxy group,
with an activated carboxylic acid derivative of the formula

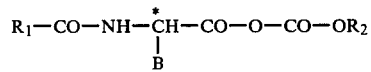

in which
 $R_1$ is an organic radical,
 B is an optionally substituted phenyl, cyclohexadienyl or heterocyclyl radical and
 $R_2$ is a lower alkyl radical, the improvement which comprises effecting the reaction in an acetone/water mixture which contains acetone and water in a volume ratio of about 0.5:1 to 3:1. Advantageously the reaction is carried out at about −10° to +10° C. in the presence of an organic base employing about 1.1 to 1.2 mols of the amino compound per mol of the activated carboxylic acid derivative.

7 Claims, No Drawings

PRODUCTION OF SEMI-SYNTHETIC β-LACTAM ANTIBIOTICS

The present invention relates to a new chemically unobvious process for the production of known semi-synthetic β-lactam antibiotics.

According to the present invention, we provide a process in which an amino compound of the general formula

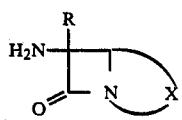
(I)

in which
X denotes the remaining members of a ring of a β-lactam antibiotic and
R denotes a hydrogen atom or a methoxy group, is reacted with an activated carboxylic acid derivative of the general formula

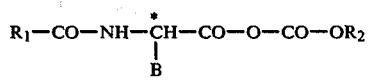
(II)

in which
R₁ denotes an organic radical,
B denotes an optionally substituted phenyl, cyclohexadienyl or heterocyclyl radical and
R₂ denotes a lower alkyl radical with 1-6 C-atoms in an acetone/water mixture which contains acetone and water in the ratio by volume of about 0.5:1 to 3:1.

It is known, for example from DE-OS (German Published Specification) No. 2,519,400, to react compounds of the formula (I) with compounds of the formula (II) in anhydrous acetone to give semi-synthetic β-lactam antibiotics. However, in this process, from the compounds of the formula (II), which are originally optically pure with regard to the chirality center characterized by *, end products are obtained which have undergone partial racemization at the chirality center.

Since, however, optically pure end products are considerably more valuable for pharmacological reasons, because they exhibit a higher action and less side effects, there is a need to alter the prior art process described above in a manner such that partial racemization at the chirality center does not occur.

An improved process according to the present invention, surprisingly, can give products which no longer have the above-mentioned disadvantages and have good optical purity.

The process is particularly suitable for the preparation of compounds of the above-mentioned optical purity of the general formula

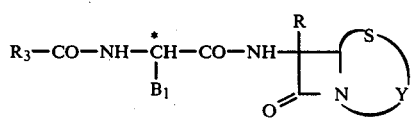
(III)

in which
R denotes a hydrogen atom or a methoxy group,
R₃ denotes a radical of the general formula

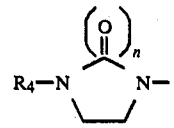

R₄ denotes a hydrogen atom or an alkyl, aryl, hetaryl, cycloalkyl, alkylsulphonyl, arylsulphonyl, hetarylsulphonyl, cycloalkylsulphonyl, alkylmethylimino, arylmethylimino, hetarylmethylimino or cycloalkylmethylimino group,
B₁ denotes a phenyl, 4-hydroxyphenyl 2-furyl or 2-amino-1,3-thiadiazol-4-yl radical,
n is 1 or 2,
Y denotes a group of the formula

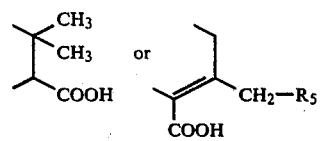

R₅ denotes a hydrogen atom, or an acetoxy, —O—CO—NR₆R₇ or

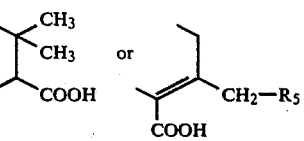 group,

R₆ and R₇ independently denote a hydrogen atom or an alkyl or cycloalkyl radical.
R₈ denotes a hydrogen atom or a carboxyl, sulpho or CH₂—NR₉R₁₀ radical and
R₉ and R₁₀ independently denote a hydrogen atom or an C₁-C₄-alkyl group.
Compounds
in which
R₄ denotes a hydrogen atom or a methylsulphonyl, cyclopropyl or (fur-2-yl)-methylimino group,
R₅ denotes a hydrogen atom, an acetoxy group or a radical of the general formula

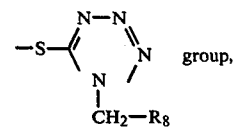

R₈ denotes a hydrogen atom or a carboxyl group and R, B₁, n and Y have the above-mentioned meaning, are preferred compounds prepared by the process according to the invention.

Compared with the process of the state of the art, which is described above, and compared with processes, which are likewise already known, in which compounds of the formula

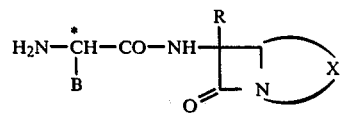
(IV)

wherein

B, R and X have the above-mentioned meaning, are reacted with activated carboxylic acids of the formula $R_1$—COOH wherein $R_1$ has the above-mentioned meaning, the process according to the invention is distinguished by a shortening of the reaction path and less effort.

Intermediate products required for the process according to the invention are known and are available by a customary method.

If B or $B_1$ denotes hydroxyphenyl, however, the corresponding compound of the formula II is appropriately prepared by silylating (4-hydroxyphenyl)-glycine and reacting the product with $R_1$—COCl and water.

The process is preferably carried out by a procedure in which the compounds of the formula (I) and the compounds of the formula (II) are reacted with one another in an acetone/water mixture at temperatures of about −60° C. to +30° C., more preferably about −10° C. to +10° C., preferably in the presence of a organic base and preferably under normal pressure. Preferably about 1 to 1.5, more preferably about 1.1 to 1.2, mols of the compound of the formula (I) are employed per one mol of the compound of the formula (II).

Possible organic bases are, in particular, secondary and tertiary amines, such as dimethylamine, triethylamine or N-methylmorpholine, or aminoalcohols. 3-Dimethylaminopropanol is preferably used. About 0.001 to 0.01 mol of the organic base are employed per mol of the compound (II).

The process according to the invention is carried out with intensive thorough mixing and has ended after about 20 to 60 minutes.

For working up, the mixture is acidified rapidly with mineral acid, for example with hydrochloric acid, whereupon the desired product crystallizes out in a very pure form. The purity of the product can be determined by various analytical methods, such as NMR spectroscopy, high pressure liquid chromatography, microbiological activity, determination of the optical rotation and circular dichroism.

The process according to the invention can be carried out in the same reaction vessel in which the compound (II) required as a precursor is prepared.

The process according to the present invention will now be illustrated by the following Examples:

EXAMPLE 1

(a) D-α-[(2-Oxo-1-imidazolinyl)-carbonyl-amino]-phenylacetic acid

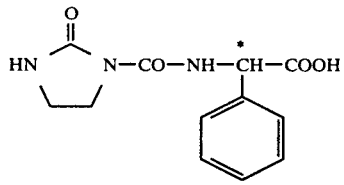

136 g of D-phenylglycine (2) are dissolved, at pH 12, in 2 l of water with 450 ml of 2 N NaOH at room temperature. The solution is then adjusted to pH 7.6 with 450 ml of 2 N HCl, while cooling. (2) precipitates again in a finely divided form. 132 g of 1-chlorocarbonyl-imidazolidinone (3) are added to the suspension and the mixture is adjusted to pH 7.7 with 810 ml of 2 N NaOH, while cooling to 20° C. After 15 minutes, most of the acid chloride has reacted. The mixture is filtered and the filtrate is brought to pH 2 with 2 N HCl. A colorless precipitate separates out. The mixture is subsequently stirred for 20 minutes and the precipitate is filtered off and washed twice with 100 ml of water. The residue on the filter is dried at room temperature in vacuo. 176 g (75% of theory) of the compound (1) with a content of 98% are obtained.

NMR: $d_6$-DMSO: δ-scale (δ: number of protons; type of signal and position of protons; coupling constant J [Hz]): 3.31, 2, t, 4—$CH_2$; 3.7, 2, t, 5—$CH_2$, $J_{4-5}=8.0$; 5.29, 1, d, α-H, $J_{α-N}=8.0$; 7.33, 5, S(b), phenyl; 7.58, 1, S, NH (imidazolidinone); and 9.05, 1, d, NH.

(b) 7.6 ml of triethylamine are added to 14.5 g of (1) in 112 ml of anhydrous acetone. The internal temperature of the mixture is kept between 20° and 25° C. After 10 minutes, a white precipitate has formed.

The mixture is cooled to −40° C. and 0.13 ml of 3-dimethylaminopropan-1-ol and 5.5 ml of chloroformic acid ethyl ester are added. The temperature of the mixture rises to −30° C. The mixture is subsequently stirred at this temperature for 10 minutes and then cooled again to −50° C. The compound of the formula

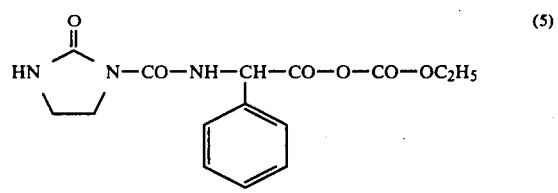

is formed.

Instead of the triethylammonium salt obtained from (1), it is also possible to prepare and use the corresponding sodium salt, which is obtained by dissolving (1), at pH 7.5, with 1 N NaOH and subsequent lyophilization.

(c) D-α-[2-Oxo-1-imidazolidinyl)-carbonyl-amino]-benzylpenicillin

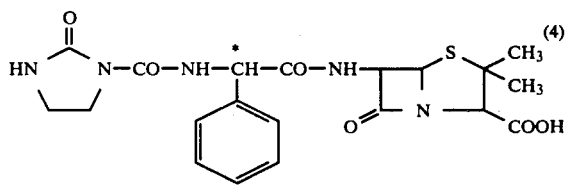

13.1 g of 6-APA are dissolved, at pH 7.8, in 38 ml of water with about 30 ml of 2 N NaOH at 0° to 5° C. in the course of about 20 minutes. The aqueous solution is added dropwise to 53 ml of acetone, which has been cooled to −20° C. The mixture is stirred for 5 minutes and at the same time adjusted to −10° C. This solution is added to the acetone solution of (5) in one operation. The internal temperature is allowed to rise to 0° C. A clear solution is formed. After adding 200 ml of water, the acetone is evaporated off in vacuo, the solution which remains is filtered and the filtrate is adjusted to pH 2 with about 70 ml of 1 N HCl The acid (4) precipitates. The colorless precipitate is filtered off, washed twice with 50 ml of water each time and dried over $P_2O_5$ in vacuo. 23 g (91% of theory) with a content of 95.5% are obtained. $[α_D]=201°$ (1% strength solution in dimethylformamide) and 187° (1% strength solution in phosphate buffer at pH 8)

EXAMPLE 2

(a) The sodium salt of D-2-[3-(methylsulphonyl)-2-oxo-imidazolidine-1-carboxamido]-2-phenylacetic acid

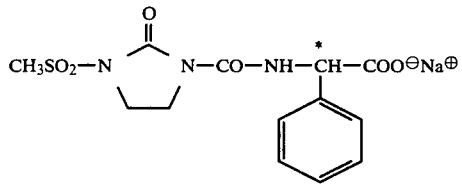
(6)

37.1 g of (2) are dissolved, at pH 12, in 545 ml of water by adding 125 ml of 2 N NaOH. (2) is precipitated again, in a finely divided form, from the solution by adjusting the pH to 7.6 with 120 ml of 2 N HCl. 60.7 g of the compound of the formula

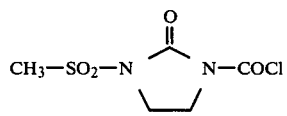
(7)

are added to the suspension, which has been cooled to 20° C. 460 ml of 1 N NaOH are added in the course of about 1 hour in a manner such that a pH of 7.6 is not exceeded. At the end of the addition, the solution is almost clear. Small amounts of solids are removed by filtration. The free acid of the salt (6) is separated out, as a colorless precipitate, from the filtrate by acidifying to pH 2 with about 240 ml of 1 N HCl. The precipitate is filtered off, washed twice with 100 ml of water and then worked up to give the Na salt by suspending in 100 ml of water, simultaneously adding 2 N NaOH, at pH 7.6, dropwise, filtering off and then lyophilizing. 49 g (55% of theory) with a content of 94% are obtained.

(b) 6-{-D-2-[3-(Methylsulphonyl)-2-oxo-imidazolidine-1-carboxamido]-2-phenyl-acetamido}-penicillanic acid

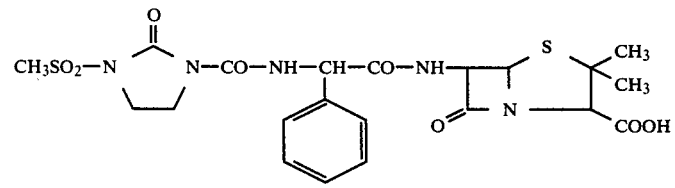
(8)

112 ml of anhydrous acetone are cooled to −40° C. and 5.5 ml of chloroformic acid ethyl ester, 0.13 ml of 3-dimethylaminopropan-1-ol and 21 g of (6) are added successively. After removing the cooling bath, the internal temperature rises to −30° C. After subsequently stirring the mixture at −30° C. for 10 minutes, it is cooled again to −50° C. An aqueous-acetone solution of sodium 6-APA is then added to the mixture, prepared by dissolving at pH 7.8, 13.1 g of 6-APA in 37 ml of water, which has been cooled to 0° C., by adding 30 ml of 2 N NaOH dropwise, and adding this solution to 53 ml of acetone, which has been cooled to −20° C., and subsequently stirring the mixture at −15° C. to −10° C. until a clear solution has formed.

After adding the solution of the Na salt of 6-APA, the internal temperature of the mixture is allowed to rise to 0° C., 200 ml of water are added and the acetone is evaporated off in vacuo at 20° to 30° C. The turbid solution which remains is adjusted to pH 7 with a few drops of sodium hydroxide solution and is filtered over kieselguhr and the filtrate is adjusted to pH 2 with about 70 ml of 1 N HCl. The colorless precipitate is filtered off, washed twice with 100 ml of water each time and dried in vacuo at 20° C. over $P_2O_5$. 25.2 g (85% of theory) with a content of 90% are obtained. $[\alpha_D] = +168°$ (1% strength in phosphate buffer at pH 8).

Instead of the Na salt (6), it is also possible to employ the triethylammonium salt, which is prepared in an acetone solution analogously to Example 1 (b)

EXAMPLE 3

(a) D-α-[3-Furfurylideneamino-2-oxo-imidazolidine-1-carboxamido]phenylacetic acid

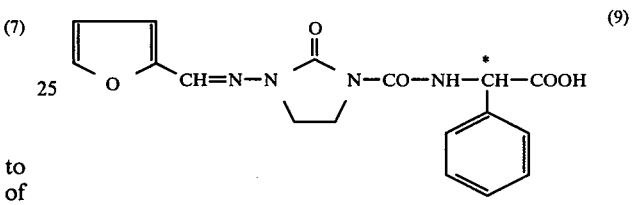
(9)

27.2 g of (2) are dissolved in 400 ml of water by adding about 95 ml of 2 N NaOH, until a pH of 12 is reached. (2) is precipitated again in a finely divided form at pH 7.6 with 15 ml of 2 N HCl. 44 g of the compound of the formula

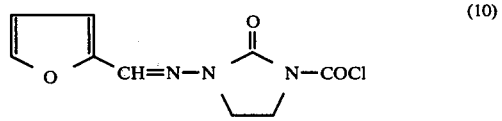
(10)

are added to the suspension. A clear solution is gradually formed by adding about 360 ml of 1 N NaOH dropwise at a pH value between 7.5 and 7.7 in the course of about 1.5 hours. Solid residues are filtered off and about 195 ml of 1 N HCl are metered into the filtrate until pH 2 is reached. The precipitate which thereby separates out is filtered off, washed twice with 200 ml of water each time and dried in vacuo at 20° C. over $P_2O_5$. 61.5 g (96% of theory) with a content of 96.4% are obtained.

NMR: 3.77, 4, s(b), $CH_2-CH_2$; 5.35, 1, d, α-H, $I_{\alpha-N}=7.5$; 6.52, 1, dd, 4-H (furane), $I_{4,5}=1.6$; 6.78, 1, d, 3-H (furane), $I_{3,4}=3.6$; 7.36, 5, s(b), phenyl; 7.68, 1, s, azomethine-H; and 7.76, 1, d, 5-H (furane).

(b) 6-{D-[3-Furfurylideneamino-2-oxo-imidazolidine-1-carboxamido]phenylacetamido}-penicillanic acid

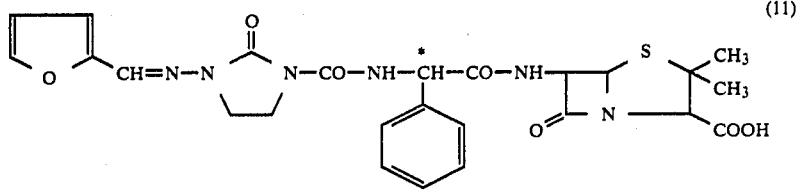

(11)

7.6 ml of triethylamine are added to 19.6 g of (9) in 280 ml of anhydrous acetone, the internal temperature being kept between 20° and 25° C. After about 2 minutes a clear solution is formed which, after subsequently stirring for a further 10 minutes, is cooled to −40° C. The triethylammonium salt separates out as a voluminous precipitate at about 0° C. 0.13 ml of 3-dimethylaminopropan-1-ol and 5.5 ml of chloroformic acid ethyl ester are added to the mixture. The mixed anhydride of the formula

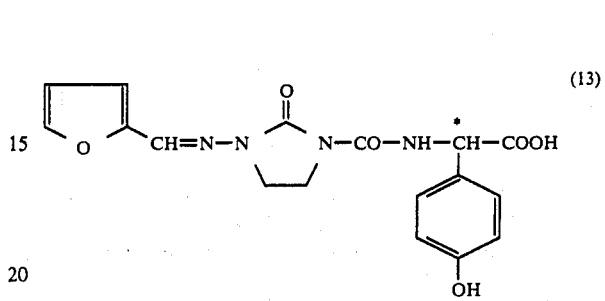

(13)

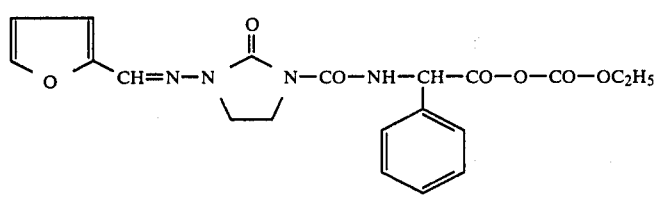

(12)

is formed. The internal temperature rises to −30° C. The mixture is subsequently stirred at this temperature for 10 minutes, whereupon it becomes more mobile.

After cooling to −50° C., an aqueous-acetone solution of the Na salt of 6-APA is added all at once, the solution being prepared by dissolving, at pH 7.5 to 7.8, 13.1 g of 6-APA in 37 ml of water, which has been cooled to 0° C., by adding 30 ml of 2 N NaOH dropwise, and adding this solution to 53 ml of acetone, which has been cooled to −20° C., and subsequently stirring the mixture at −15° to −10° C. until a clear solution has formed.

After combining the two solutions, the temperature is allowed to rise gradually to 0° C., 200 ml of water are then added and the acetone is evaporated off at 20° C. in vacuo. The solution is made up to 750 ml with water, solid residues are filtered off and the filtrate is adjusted to pH 2 with about 53 ml of 1 N HCl. The colorless precipitate is filtered off, washed twice with 50 ml of water each time and dried in vacuo at 20° C. over $P_2O_5$. 29 g (95% of theory) with a content of 92.5% are obtained. $[\alpha_D] = +222.6°$ (0.5% strength solution in phosphate buffer at pH 8).

Instead of the triethylammonium salt, it is also possible to employ the corresponding Na salt.

NMR: 1.47, 3, s, 2-$CH_3$; 3.85, 4, s(v), $CH_2$-$CH_2$; 3.99, 1, s, 3-H; 5.34, 1, d, 5-H, $I_{5-6}=3.9$; 5.47, 1, dd, 6-H, $I_{6-N}=8.0$; 5.78, 1, d, $\alpha$-H, $I_{\alpha-N}=8.0$; 6.64, 1, dd, 4-H (furane), $I_{4-5}=1.6$; 6.89, 1, d, 3-H (furane), $I_{3-4}=3.5$; 7.2-7.5, 5, m, phenyl; 7.78, 1, s, azomethine-H; 7.84, 1, d, 5-H (furane); 9.08, 1, d, 6-N-H; and 9.15, 1, d, $\alpha$-N-H.

EXAMPLE 4

(a) D-$\alpha$-[3-Furfurylidene-2-oxo-imidazolidine-1-carboxamido]-p-hydroxy-phenylacetic acid 76.8 g of trimethylchlorosilane (15) dissolved in 100 ml of $CH_2Cl_2$, are added dropwise to 33.4 g of D-p-hydroxy-phenylglycine (14) and 91.2 g of triethylamine in 420 ml of $CH_2Cl_2$ at room temperature, while cooling with water (internal temperature: 20° to 25° C.), in the course of 30 minutes.

Thereafter, the mixture is stirred overnight, without being heated. A light beige suspension is formed. About 360 ml of $CH_2Cl_2$ are distilled off under normal pressure, the mixture is cooled to 20° C. and the triethylammonium hydrochloride which has precipitated is filtered off. The residue on the filter is washed twice with 80 ml of $CH_2Cl_2$ each time and the wash liquor is combined with the filtrate. 48.5 g of (10) are introduced, in portions, into the filtrate in the course of 30 minutes, while cooling. The internal temperature is 20° to 25° C. After the addition a brown-black solution is present. The solution is subsequently stirred for 15 minutes and then evaporated to dryness in vacuo at 20° C.

The residue is dissolved in 400 ml of anhydrous acetone and the solution is stirred with 15 g of active charcoal for 5 minutes and filtered over an AS filter.

The clear brown solution is allowed to run into 600 ml of water, while stirring vigorously, and the mixture is subsequently stirred for 10 minutes, during which a colorless precipitate which is initially amorphous, then crystalline to an increasing extent, is formed and is filtered off. The residue on the filter is rinsed twice with 100 ml of water each time and then twice with 50 ml of acetone each time and dried in vacuo at 20° C. over $P_2O_5$. 68.5 g (92% of theory) with a content of 94.0% are obtained.

NMR: 3.77, 4, s(b), $CH_2$—$CH_2$; 5.19, 1, d, $\alpha$-H, $I_{\alpha-N}=7.5$; 6.55, 1, dd, 4-H (furane), $I_{4-5}=1.6$; 6.77, 2, d, 2,2'-H (phenyl), $I_{2-3}=8.5$; 6.82, 1, d, 3-H (furane), $I_{3-4}=3.5$; 7.1, 2, d, 3,3'-H (phenyl); 7.7, 1, s, azomethine-H;

7.77, 1, d, 5-H (furane); 8.95, 1, d, N-H; and 9.5, 1, s(b), COOH.

(b) 6-{D-α-[3-Furfurylideneamino-2-oxo-imidazolidine-1-carboxamido]}-p-hydroxy-phenyl-acetamido-penicillanic acid 6.64, 1, dd, 4-H (furane), $I_{4,5}=1.6$; 6.77, 2, d, 2,2'-H (phenyl), $I_{2,3}=8.5$; 6.87, 1, d, 3-H (furane), $I_{3,4}=3.6$; 7.23, 2, d, 3,3'-H (phenyl); 7.7, 1, s, azomethine—H; 7.84, 1, d, 5-H (furane); 8.96, 1, d, 6-NH; and 8.99, 1, d, α-N-H.

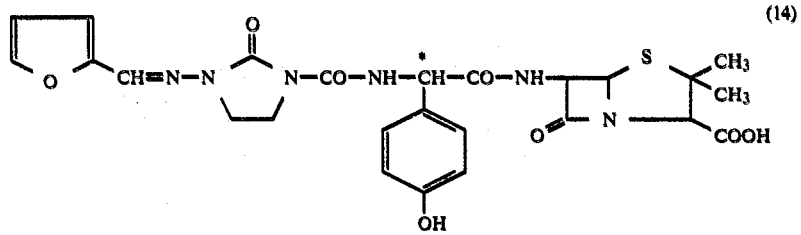

(14)

7.6 ml of triethylamine are added to 20.4 g of (13) in 280 ml of anhydrous acetone, with exclusion of moisture. After about 3 minutes, conversion into the triethylamine salt, which can be recognized by the formation of a finely divided voluminous precipitate, begins.

After subsequently stirring the mixture for 10 minutes, it is cooled to −10° C. 0.13 ml of 3-dimethylaminopropanol and 5.5 ml of chloroformic acid ethyl ester are then added to the mixture. The temperature thereby increases to 0° C. The mixture gradually becomes more mobile in the course of 45 minutes. The mixed anhydride of the formula

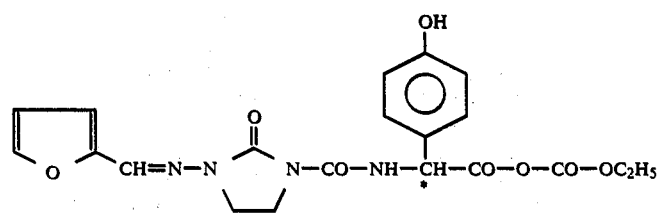

is formed. Thereafter, the mixture is cooled again to −10° C. and an aqueous-acetone solution of the Na salt of 6-APA is added, the solution being prepared by dissolving 13.1 g of 6-APA in 37 ml of water, which has been cooled to 0° C., at pH 7.5–7.8 by adding 30 ml of 2 N NaOH dropwise, and adding this solution to 53 ml of acetone, which has been cooled to −20° C., and subsequently stirring the mixture at −15° C. to −10° C. until a clear solution has formed. After combining the mixtures, the temperature was kept at −10° C. and the mixture is subsequently stirred for 1 hour. The internal temperature is then allowed to rise to −5° C. and the mixture is acidified rapidly to pH 2 with about 70 ml of 1 N HCl. The mixture thereby becomes clear for a short time. A few minutes after the final pH is reached, the crystalline acid starts to precipitate. The mixture is subsequently stirred for 1 hour and the colorless precipitate is then filtered off. The filter cake is washed twice with 100 ml of water each time and sucked dry for 30 minutes. It is then dried to constant weight in vacuo at 20° C. over phosphorus pentoxide.

Yield: 25 g=79% of theory.
Content: 96%
$[\alpha_D] = +233°$ (1% strength solution in phosphate buffer at pH 8)

Instead of the triethylammonium salt, it is also possible to employ the corresponding Na salt.

NMR: 1.47, 3, s, 2—CH₃; 1.59, 3, s, 2—CH₃; 3.84, 4, s(b), CH₂—CH₂; 3.95, 1, s, 3-H; 5.35, 1, d, 5-H, $I_{5-6}=3.9$; 5.47, 1, dd, 6-H, $I_{6-N}=8.0$; 5.65, 1, d, α-H, $I_{\alpha-N}=8.0$;

It will be appreciated that the instant specification and examples are set forth by way of illustration and not limitation, and that various modifications and changes may be made without departing from the spirit and scope of the present invention.

What is claimed is:

1. In the production of a semi-synthetic β-lactam antibiotic by reacting an amino compound of the formula

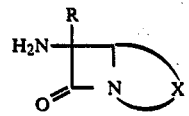

in which
X is the remaining members of a ring of a β-lactam antibiotic, and
R is a hydrogen atom or a methoxy group,
with an activated carboxylic acid derivative of the formula

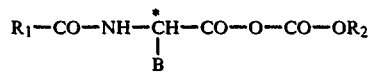

in which
R₁ is an organic radical,
B is an optionally substituted phenyl, cyclohexadienyl or heterocyclyl radical and
R₂ is a lower alkyl radical,
the improvement which comprises effecting the reaction in an acetone/water mixture which contains acetone and water in a volume ratio of about 0.5:1 to 3:1.

2. A process according to claim 1, in which the semi-synthetic β-lactam antibiotic produced is a compound of the formula

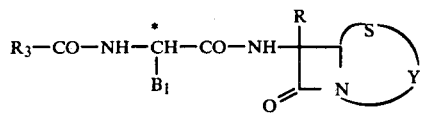

in which

R₃ is a radical of the formula

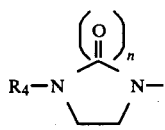

R₄ is a member selected from the group consisting of a hydrogen atom, an alkyl, aryl, hetaryl, cycloalkyl, alkylsulphonyl, arylsulphonyl, hetarylsulphonyl, cycloalkylsulphonyl, alkylmethylimine, arylmethylimino, hetarylmethylimino and cycloalkylmethylimino group, B₁ is a phenyl, 4-hydroxyphenyl, 2-furyl or 2-amino-1,3-thiadiazol-4-yl radical, n is 1 or 2, Y is

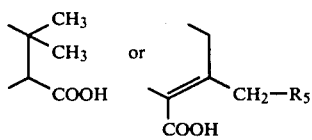

R₅ is a member selected from the group consisting of a hydrogen atom, an acetoxy radical, a —O—CO—NR₆R₇ radical and a

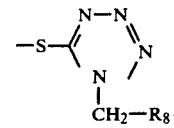

radical,

R₆ and R₇ each independently is a member selected from the group consisting of a hydrogen atom, an alkyl radical and a cycloalkyl radical, R₈ is a hydrogen atom, carboxyl, sulpho or CH₂-NR₉R₁₀ radical, and R₉ and R₁₀ each independently is a hydrogen atom or an alkyl group.

3. A process according to claim 2, in which

R₄ is a member selected from the group consisting of a hydrogen atom, a methylsulphonyl, cyclopropyl and (fur-2-yl)-methylimino group, R₅ is a hydrogen atom, an acetoxy group or a radical of the formula

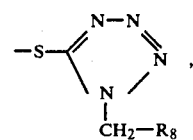

and

R₈ is a hydrogen atom or a carboxyl group.

4. A process according to claim 1, in which the reaction is carried out at about −60° C. to +30° C.

5. A process according to claim 1, in which the reaction is carried out in the presence of an organic base.

6. A process according to claim 1, in which about 1 to 1.5 mols of the amino compound are employed per mol of the activated carboxylic acid derivative.

7. A process according to claim 3, in which the reaction is carried out at about −10° to +10° C. in the presence of an organic base employing about 1.1 to 1.2 mols of the amino compound per mol of the activated carboxylic acid derivative.

* * * * *

UNITED STATES PATENT AND TRADEMARK OFFICE
CERTIFICATE OF CORRECTION

PATENT NO. : 4,229,349

DATED : Oct. 21, 1980

INVENTOR(S) : Werner Ertel

It is certified that error appears in the above-identified patent and that said Letters Patent are hereby corrected as shown below:

Column 11 Line 24 delete "alkylmethylimine" and
insert -- alkylmethylimino --

Signed and Sealed this

Twenty-first Day of April 1981

[SEAL]

Attest:

RENE D. TEGTMEYER

Attesting Officer

Acting Commissioner of Patents and Trademarks